United States Patent [19]

Nepon

[11] 4,436,723

[45] Mar. 13, 1984

[54] ARTHRITIS COMPOSITION OF MATTER, AND METHODS OF PREPARING AND UTILIZING SAME

[76] Inventor: Juanita Nepon, 21640 Twelve Mile Rd., St. Clair Shores, Mich. 48081

[21] Appl. No.: 190,457

[22] Filed: Sep. 24, 1980

[51] Int. Cl.[3] ..................... A61K 35/12; A61K 35/28; A61K 35/407
[52] U.S. Cl. ..................................... 424/95; 424/106
[58] Field of Search ........................ 424/106, 101, 95

[56] References Cited

FOREIGN PATENT DOCUMENTS 2426584  1/1975  Fed. Rep. of Germany ...... 424/106
696178  8/1953  United Kingdom ................ 424/106

OTHER PUBLICATIONS

Schneider et al.—Chem. Abst., vol. 32, (1938), p. 5453[9].
Unlisted Drugs, vol. 20, No. 7, Jul. 1968, p. 105.
Dictionaire Vidal—1961, p. 1581.
Remington's Practice of Pharmacy, 9th Edit., (1948), pp. 1288 and 1289.
Bollet—Chem. Abst., vol. 73, (1970), p. 129243t.
Tuccimei—Chem. Abst., vol. 49, (1955), p. 1200b.
Guglielmi et al., Chem. Abst., vol. 72, (1970), p. 99038q.
Forbes—Chem. Abst., vol. 21, (1927), pp. 3935 bottom, 3936 top.
Krauss—Chem. Abst., vol. 12, (1918), p. 1572[2].

*Primary Examiner*—Sam Rosen
*Attorney, Agent, or Firm*—Irving M. Weiner; Pamela S. Burt; John L. Shortley

[57] ABSTRACT

A composition including edible bone meal with red bone marrow and desiccated beef liver mixed in predetermined proportions. The composition may be provided in tablet form, and is adapted to be taken orally by persons suffering from arthritic pain to thereby provide relief of such pain.

3 Claims, No Drawings

ARTHRITIS COMPOSITION OF MATTER, AND METHODS OF PREPARING AND UTILIZING SAME

BACKGROUND OF THE INVENTION

1. Field of the Invention

The present invention relates to a novel composition which is particularly adapted for the treatment of arthritis and which may be taken orally by a person afflicted with arthritis to thereby provide relief from arthritic pain. The invention also relates to methods of preparing the aforementioned composition.

2. Description of Relevant Art

As is well known in the medical field, and more particularly by persons suffering with arthritic conditions, the treatment of arthritis to alleviate the ofttimes agonizing pain associated therewith has heretofore met with only minimal success. Although various known aspirin products and other medications have heretofore been available for use by arthritic sufferers, such products and/or medications have generally proven unsatisfactory in providing effective relief from the pain associated with the inflammatory joint conditions of arthritis.

The present invention provides a novel composition for the treatment of arthritis which is particularly directed towards substantially alleviating the pain associated with arthritic conditions. The novel composition in accordance with the invention comprises a mixture of bone meal with red bone marrow and desiccated beef liver, such ingredients being mixed together in predetermined proportions to provide a highly effective pain-reducing composition for the treatment of arthritis.

Illustrative of a known pharmaceutical product which includes liver as an ingredient thereof is that disclosed in U.S. Pat. No. 2,901,396 issued in 1959 to Lewis et al entitled "PREPARATION OF PHARAMCEUTICAL LIVER PRODUCTS." The disclosure of such patent is particularly directed toward a technique for preparing pharmaceutical liver liquids having sufficient stability to prolong the shelf life thereof. Lewis et al is not at all concerned with the treatment of arthritis, and moreover generally fails to disclose a composition comparable to that of the present invention.

The novel composition in accordance with the present invention is directed toward providing effective relief from the pain associated with the inflammation of the joints of arthritic sufferers.

SUMMARY OF THE INVENTION

The present invention provies a composition which comprises as the basic ingredients thereof edible bone meal and desiccated liver, such composition being particularly useful in treatment of arthritis. The edible bone meal employed in preparing the composition comprises sterilized cattle bone meal which includes red bone marrow, and the desiccated liver comprises substantially non-defatted beef liver. The proportions of edible bone meal with red bone marrow and desiccated beef liver in the composition is substantially eight parts edible bone meal with red bone marrow to five parts desiccated beef liver.

Preferably, the composition is provided in individual tablet portions adapted to be taken orally by a user thereof. Each such tablet includes substantially eight milligrams of the edible bone meal with red bone marrow and five milligrams of the desiccated beef liver.

It is a primary object of the present invention to provide a novel composition for the effective treatment of arthritis which provides substantial, if not complete, relief of the pain normally experienced by arthritic sufferers.

The present invention further provides a method for preparing the aforesaid composition, comprising the steps of: combining the edible bone meal with red bone marrow and desiccated beef liver, mixing such dry mixture with water so as to form a paste, forming the paste into individual tablet-shaped portions, and drying the tablets by cooking same at approximately 150° F. for approximately ten minutes.

Other objects and details of the invention will become apparent from the following detailed description.

DETAILED DESCRIPTION OF PREFERRED EMBODIMENTS

The novel composition in accordance with the present invention includes as the basic ingredients thereof edible bone meal and desiccated liver.

Preferably, the edible bone meal employed in the composition comprises natural cattle bone meal which is sterilized under controlled heat conditions to preserve all the natural elements thereof, and which includes red beef bone marrow. Bone meal of the aforesaid type is readily commercially available, and may include natural additives such as fish liver oils, for example.

The desiccated liver employed in the composition of the present invention preferably comprises natural desiccated (low heat dried) beef liver, which may preferably be non-defatted, and which is also readily commercially available.

In accordance with the invention, the foregoing ingredients, i.e., edible bone meal with red bone marrow and desiccated beef liver, are combined in proportions of substantially eight parts by weight of edible bone meal with red bone marrow to substantially five parts by weight of desiccated beef liver. The resulting composition will be very high in calcium, phosphorus and zinc content, and will also contain a variety of other nutrients such as Vitamin B-1, Vitamin B-2, Vitamin B-12, Folic Acid, Iron, etc.

In preparing the composition in accordance with the invention, the edible bone meal with red bone marrow and the desiccated beef liver, both in dry form (i.e., powdered), are combined in the aforesaid proportions and are mixed with water until a paste-like consistency is obtained. Such paste is then formed into individual tablet-shaped portions, such as with a suitable mold or any other suitable means, each individual tablet preferably containing eight milligrams of the bone meal with red bone marrow and five milligrams of the desiccated beef liver. The tablets are thereafter placed in an oven (or other suitable heating means) at a temperature of approximately 150° F. for a period of approximately ten minutes to effect drying thereof.

The tablets obtained in accordance with the foregoing method are particularly useful in the treatment of arthritis, and are adapted to be taken orally to substantially alleviate the pain associated with the inflammatory joint conditions of arthritis.

Although not specifically disclosed hereinabove, it is further contemplated that various additives or excipients may be added to the aforesaid composition as desired. Further, although the composition has been described hereinabove as provided in tablet form, it is contemplated that, if desired, the composition may be provided in other convenient forms, such as capsules.

Although there have been described what are at present considered to be the preferred embodiments of the invention, it will be understood that various modifications may be made therein without departing from the spirit or essential characteristics thereof. The present embodiments are therefore to be considered in all respects as illustrative, and not restrictive. The scope of the invention is indicated by the appended claims rather than by the foregoing description.

I claim:

1. A composition for use in treating arthritis comprising:
   dried edible natural bone meal;
   said bone meal comprising red bone marrow; and natural desiccated beef liver;
   said bone meal and said desiccated liver being mixed with water;
   the relative proportion of edible bone meal to liver being approximately eight parts bone meal to five parts liver.
2. The composition of claim 1, wherein:
   said bone meal comprises cattle bone meal; and
   said liver comprises beef liver.
3. The composition of claim 1 wherein said bone meal and said dessicated liver have been mixed with water to form a paste and then dried by heating at approximately 150° F.

* * * * *